(12) United States Patent
Todd et al.

(10) Patent No.: US 9,753,026 B1
(45) Date of Patent: Sep. 5, 2017

(54) CELL PROCESSING CARTRIDGE FOR MINIATURE CYTOMETER

(71) Applicant: Techshot, Inc., Greenville, IN (US)

(72) Inventors: Paul W. Todd, Greenville, IN (US); Todd Fricke, New Albany, IN (US); Scott Moyers, New Albany, IN (US)

(73) Assignee: Techshot, Inc., Greenville, IN (US)

( * ) Notice: Subject to any disclaimer, the term of this patent is extended or adjusted under 35 U.S.C. 154(b) by 223 days.

(21) Appl. No.: 14/144,446

(22) Filed: Dec. 30, 2013

Related U.S. Application Data

(60) Provisional application No. 61/747,396, filed on Dec. 31, 2012, provisional application No. 61/762,677, filed on Feb. 8, 2013.

(51) Int. Cl.
*B01L 3/00* (2006.01)
*G01N 33/50* (2006.01)

(52) U.S. Cl.
CPC ................ *G01N 33/5094* (2013.01)

(58) Field of Classification Search
CPC ............ B01L 3/5027; B01L 3/502738; B01L 3/502715; B01L 2300/0819; B01L 2300/0867; B01L 2400/0487; B01L 2400/0622; B01L 2400/0644; G01N 33/4915; G01N 1/38; G01N 2035/00237
See application file for complete search history.

(56) References Cited

U.S. PATENT DOCUMENTS

| 5,199,576 A | 4/1993 | Corio et al. |
| 5,204,884 A | 4/1993 | Leary et al. |
| 5,550,058 A | 8/1996 | Corio et al. |
| 5,804,143 A | 9/1998 | Leary et al. |
| 5,998,212 A | 12/1999 | Corio et al. |

(Continued)

OTHER PUBLICATIONS

Grafton, Meggie, et al. "Design of a multi-stage microfluidics system for high-speed flow cytometry and closed system cell sorting for cytomics." Biomedical Optics (BiOS) 2008. International Society for Optics and Photonics, 2008.

(Continued)

*Primary Examiner* — Brian R Gordon
(74) *Attorney, Agent, or Firm* — Middleton Reutlinger; Robert H. Eichenberger; Chad D. Bruggeman

(57) ABSTRACT

The present embodiment relates to a miniaturized single-use apparatus for the preparation and analysis of suspensions of cells for flow cytometry. The cartridge apparatus is a unique combination, in order of function, of a miniature single-drive, two-cylinder syringe pump, a dual-channel stopcock valve that also performs volumetric measuring functions, a capillary-based fluid loading and measuring method, a miniaturized multistage interfacial-surface-generator mixer, a microfluidic magnetic cell selector, branching microfluidic channels with widths determined according to function, enclosed absorption-based disposal of potentially biohazardous liquids and a design compatible with manufacturing as a single-use device. In one embodiment the device for processing and labeling samples processes and samples small volumes, such as a drop of blood. The device can exist in hand-held versions, hand-carried versions and bench-scale versions of optical reading devices for flow cytometry.

12 Claims, 6 Drawing Sheets

(56) References Cited

U.S. PATENT DOCUMENTS

| | | | |
|---|---|---|---|
| 6,989,129 B2* | 1/2006 | Licklider | G01N 30/08 |
| | | | 210/198.2 |
| 7,214,320 B1* | 5/2007 | Gregori | B01L 3/502753 |
| | | | 210/143 |
| 7,452,725 B2 | 11/2008 | Leary et al. | |
| 7,687,269 B2* | 3/2010 | Kautz | B01L 3/502784 |
| | | | 422/502 |
| 8,012,432 B2* | 9/2011 | Berndtsson | B01L 3/502 |
| | | | 422/501 |
| 8,096,421 B2 | 1/2012 | Shinoda | |
| 8,246,805 B2 | 8/2012 | Shinoda | |
| 8,377,395 B2* | 2/2013 | Coleman | B01L 3/50215 |
| | | | 210/121 |
| 8,449,830 B2* | 5/2013 | Claussen | B01L 3/502753 |
| | | | 422/129 |
| 8,657,121 B2 | 2/2014 | Shinoda et al. | |
| 8,697,010 B2* | 4/2014 | Kanai | B01L 3/0293 |
| | | | 422/503 |
| 8,795,500 B2 | 8/2014 | Shinoda | |
| 2002/0166592 A1* | 11/2002 | Liu | G01N 27/44743 |
| | | | 137/825 |
| 2004/0156753 A1* | 8/2004 | Roitman | B01J 19/0093 |
| | | | 422/504 |
| 2006/0216213 A1* | 9/2006 | Biwa | B01L 3/502715 |
| | | | 422/400 |
| 2007/0269345 A1* | 11/2007 | Schilffarth | G01N 15/1484 |
| | | | 422/73 |

OTHER PUBLICATIONS

Grafton, Meggie M., et al. "Microfabrication of a two-stage BioMEMS microfluidic cell sorter." SPIE MOEMS-MEMS: Micro- and Nanofabrication. International Society for Optics and Photonics, 2009.

Bassler, M.; Kiesel, P.; Beck, M.; Schmidt, O.; Hegyi, A.; Buergel, T.; Johnson, N. M. A novel concept for on-chip flow cytometry with improved signal-to-noise-ratio and "alignment-free" optics. XXIV International Congress of the International Society for Analytical Cytometry; May 17-21, 2008; Budapest, Hungary.

Pamme N, Wilhelm C. Continuous sorting of magnetic cells via on-chip free-flow magnetophoresis. Lab on a Chip. 6: 974-980. Aug. 1, 2006.

Shinoda, M., G. Hashimoto, T. Takashimizu, M. Furuki, H. Nakauchi, Y. Morita and Y. Yamazaki. High throughput flow cytometry using multichannel microfluidics chip. Jan. 1, 2008.

* cited by examiner

CELL PROCESSING CARTRIDGE FOR MINIATURE CYTOMETER

CROSS-REFERENCE TO RELATED APPLICATIONS

This application claims priority to and benefit from U.S. Provisional Application No. 61/747,396, filed Dec. 31, 2012, and U.S. Provisional Application No. 61/762,677, filed Feb. 8, 2013, all of which are incorporated by reference in their entirety.

STATEMENT REGARDING FEDERALLY SPONSORED RESEARCH AND DEVELOPMENT

This invention was made with Government support under contract NNX10CB06C. The Government has certain rights in the invention.

TECHNICAL FIELD

The embodiments of the invention are in the field of cell analysis and more specifically flow cytometry. The embodiments provide automated low-volume processing and flow through an optical analysis system for the detection and counting of single cells in a microfluidic flow stream.

SUMMARY

The present embodiment facilitates the counting and characterization of biological cells in liquid suspension by the method of flow cytometry in a uniquely miniaturized format. The cell processing cartridge for miniature cytometer is a device for combining a sample of biological cells in suspension with a solution of reagents that label cells according to function, and for causing the labeled cells to flow through branching microchannels. When the cartridge is inserted into a suitable bench-scale or miniature cytometer a magnet can deflect specific cell types (such as white blood cells) into one of the channels. Also the very narrow branching channels are used to non-specifically reduce the volumetric flow to facilitate the cytometric counting of cells that may be present in high concentration (such as red blood cells). One important aspect of the cartridge resides in its unique combination of specific miniaturized technologies. It is a unique combination, in order of function, of a miniature single-drive, two-cylinder syringe pump, a dual-channel stopcock valve that also performs volumetric measuring functions, a capillary-based fluid loading and measuring method, a miniaturized multistage interfacial-surface-generator mixer, a microfluidic magnetic cell selector, branching microfluidic channels with widths determined according to function, enclosed absorption-based disposal of potentially biohazardous liquids and a design compatible with manufacturing as a single-use device.

It is desired to miniaturize aspects of flow cytometers to produce a multichannel microfluidic flow cytometer that could be used in point-of-care applications, especially in remote and/or underserved locations.

One embodiment is applied to the construction and testing of semiconductor-only optical analysis stations for single cells, development of reagents and reaction protocols for cell labeling, construction and testing of automated systems for mixing reagents and sample, assembling a lab-on-a-chip automated cartridge, and assembly of optics, electronics and mechanical components into an accompanying miniature reader. To avoid use of additional energy for mixing the small volumes involved an embodiment incorporating a miniaturized in-line microfluidic static mixer.

Within the cartridge, cells should be labeled so as to be detected by the semiconductor optical analysis stations in which signals are passed from sensitive silicon photomultipliers to noise-reducing analysis circuits and to a digital display.

One application is to use a multichannel microfluidic cytometer that could count white blood cells, red blood cells, and the following subsets: CD11B+ granulocytes/monocytes, T4 helper lymphocytes and T8 lymphocytes. These subsets are markers of immunodeficiency and are used in AIDS monitoring and astronaut health as examples of remote populations. Subsystems were developed through research and paths of discovery, such as sorting WBCs on the basis of immunomagnetic labeling and counting subsets using immunoquantum dot labeling and using a reader (not included in this embodiment) that produces fluorescence excitation using superluminescent LEDs and detection by avalanche photodiodes (aka silicon photomultipliers). Triple labeling of WBCs was demonstrated and exploited. A robust optical stack design is implemented to "read" the operating cartridge. All fluidics are incorporated into a "single use" cartridge consisting of a sample receptacle, reagent reservoir, static in-line "hybrid" mixer, and a multichannel microfluidic for guiding cells in the optical analysis paths.

The designed result is to develop a flow cytometer in which all of the components are miniaturized to achieve, as closely as possible, a hand-held status for a flow cytometer capable of at least counting subtypes of blood cells in a gravity-independent way. This is achieved by replacing hydrodynamically focused single-cell flow with microfluidics and optical emission and detection devices with semiconductor technologies. The microfluidics chip component consists of an inlet channel for the blood-reagent mixture, a magnetic deflector that drives magnetically labeled WBCs down the WBC channel, and a continuation of the inlet channel that is bifurcated 10:1 to sample the total cell count (essentially the RBC count).

BRIEF DESCRIPTION OF THE ILLUSTRATIONS

Embodiments of the invention are illustrated in the following illustrations.

DETAILED DESCRIPTION

While the present embodiment will be described more fully hereinafter with reference to the accompanying drawings in which particular embodiments and methods are shown, it is to be understood from the outset that persons of ordinary skill in the art may modify the embodiment herein described while achieving the functions and results of this embodiment. Sound engineering judgment may be used to modify various aspects and components of the embodiment without detracting from the broad, general teachings hereof. Accordingly, the description that follows is to be understood as illustrative and exemplary of specific embodiments within the broad scope of the present embodiment and not as limiting the scope of the embodiment. In the following descriptions, like numbers refer to similar features or like elements throughout.

Figure 1:
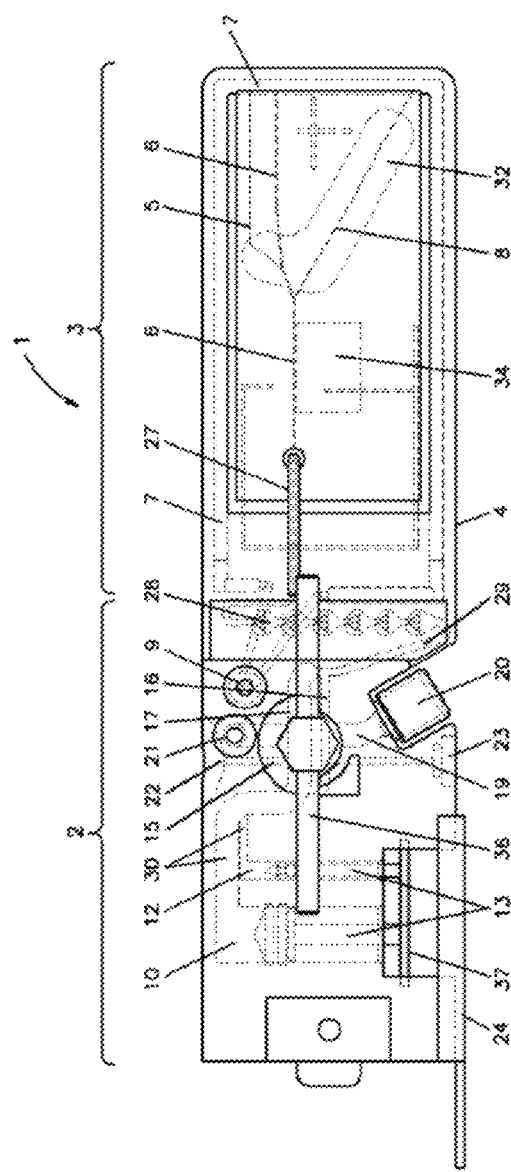
FIG. 1 is a top view of one embodiment of a cell processing cartridge.

A drawing of an example of a disposable or re-usable cartridge is seen in FIG. 1. In this particular embodiment, the disposable or re-usable cartridge 1 is composed of two parts: an up-front fluid processor 2 and a microfluidic chip 3. The up-front fluid processing unit 2 may be fabricated by rapid prototyping using, for example, Stereo Lithography Apparatus (SLA) while the microfluidic chip 3 with branching channels (on the right in the figure) is fabricated using standard molding of Polydimethylsiloxane (PDMS) against an etched SU-8 silicon mold. The microfluidic chip 3 in this embodiment is supported by a SLA frame with a thin backing that is SLA fabricated integral to the plastic processing unit 2. The microfluidic chip 3 in this embodiment is for magnetically selecting magnetically labeled cells, such as white blood cells from main channel 6 for deflection into branching channel 8, and for non-specifically deflecting 10% (for example) of the main-channel flow volume into channel 5 to count red blood cells. The effluents of all channels are deposited in a waste gutter 7, which surrounds the microfluidic chip and is vented through a filtered outlet 9. Aqueous buffer solution for pushing two flows is loaded into two cylinders, 10 and 12, respectively, all the way up to the two-channel rotating valve 15. Rotating valve 15 is a tapered solid cylinder having two channels, the narrower one of which, 16, determines the volume of blood and the other, 17 determines the volume of reagent to be combined. Reagent, consisting of a solution of magnetic and fluorescent substances that react with cells, is loaded (typically by a manufacturer) into the larger channel 17 of the rotating valve via passage 19 by injection through an elastomer septum 20 with pressure being relieved through filtered outlet 21. During loading, passage 19 is fluidically coupled to the larger channel 17 within the rotating valve, which receives the reagent solutions when in the "loading" position. The user/patient places a lancet-punctured finger at the sample inlet 22 on the side of the cartridge (indentation), and sample flows into the narrower channel 16 of the rotating valve due to capillary-driven flow with pressure relieved by sample vent 23. The rotating valve 15 is then turned 90 degrees using valve handle 36 causing both channels 16 and 17 to be fluidically coupled to the buffer solutions in cylinders 12 and 10, respectively, as shown in FIG. 1, in which the rotating valve can be considered to be in the "operating" position. An operator removes a retainer 24 by sliding it leftward (in the orientation of FIG. 1) before inserting the cartridge into the cytometer. There are stops to limit the valve 15 to only these two aforesaid positions. The rest of the process is automated and begins when the user has inserted the cartridge into a miniature cytometer 40, shown in FIG. 2, which has optical sensors spatially positioned to correspond to the dashed optically clear region 32 and a single magnet spatially positioned to correspond to the dashed region 34. Insertion of the cartridge 1 engages the cytometer's 40 operating electronics including an actuator that pushes both pistons 13 in the buffer cylinders 10 and 12 by pushing push-bar 37. Drains 7 are vented to atmosphere by means of a hydrophobic membrane at waste vent 9.

Figure 3:
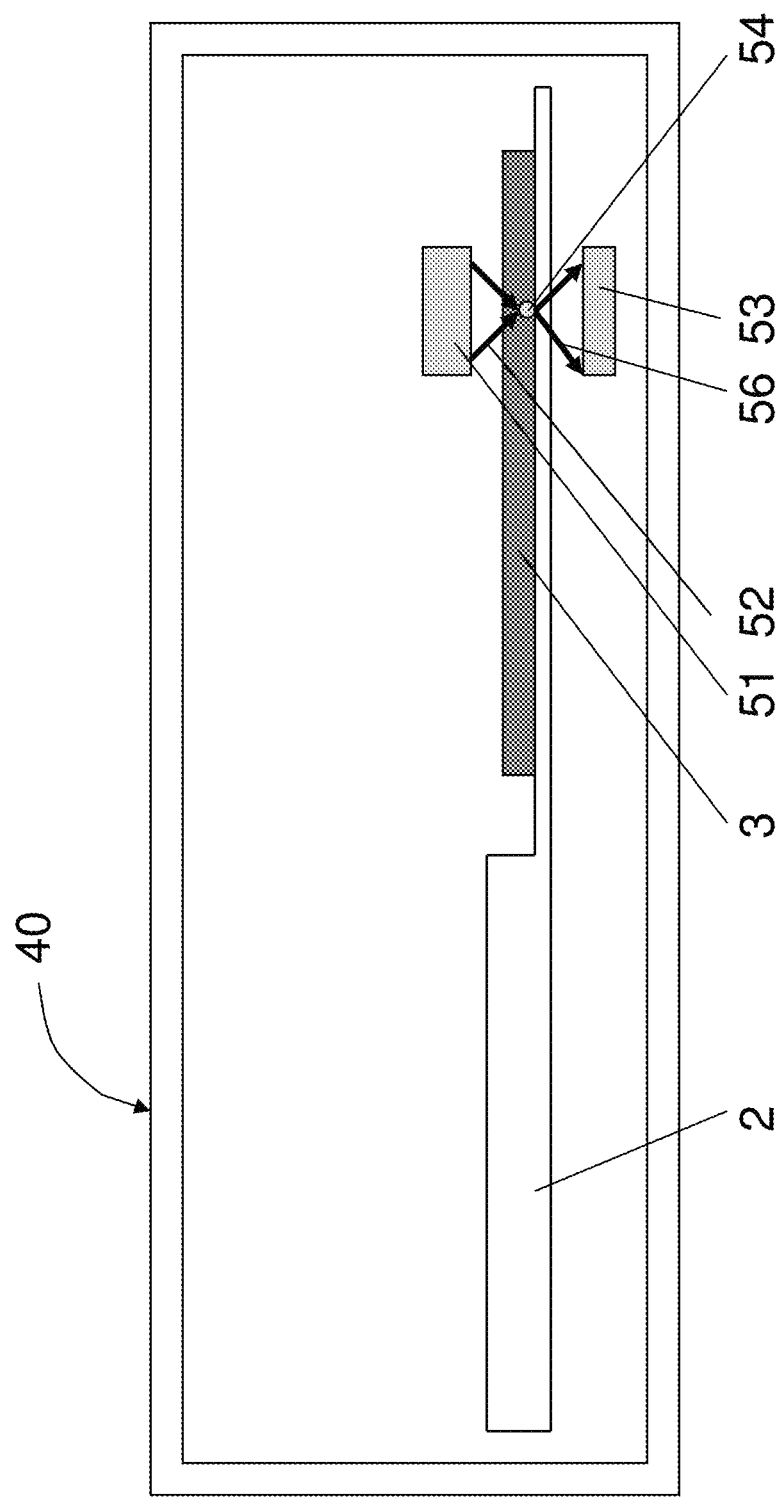
FIG. 3 is a schematic indicating how the cell processing cartridge is to be used in an optical cytometer reading device.

The rotating valve 15 is set to the "operating" position prior to insertion of the cartridge into the cytometer so that the sample and reagent are forced, side-by-side to flow into static mixer 28, which in this embodiment has 6 mixing stages and is an Interfacial Surface Generator type of mixer within a volume range of 100 to 400 µL. The driving force is the two channels of buffer flow 30 induced by the cytometer's actuator drive, which pushes two pistons in the cylinders 10 and 12 at the same velocity. The cross section of the sample channel 16 is 1/10th the cross section of the reagent channel 17 so that, for example, 1 µL of sample is combined with every 10 µL of reagent as the fluids enter the mixer 28 as they pass through channel 29. Reagent and buffer are expected to be pre-loaded prior to operation, but the user adds sample (a droplet of whole blood). Once inside the miniature cytometer 40 the cartridge is pumping cells through the channels via connecting tube 27. FIG. 3 is a drawing showing how a labeled cell 54 in a channel within the PDMS microfluidic chip 3 is in the path 52 of an illuminating light source 51, so that the scattered or fluorescent light 56 or other optical property from the cell in the channel is detected by the light sensor 53 while enclosed in the light-tight housing of 40.

The branching scheme is shown in FIG. 1 as channels 5, 6, and 8. Sample after mixing with reagent enters via transfer tube 27 at channel 6 and flows left to right through this inlet channel, which has a magnet (not shown) beside it at position 34. Magnetically labeled WBCs are deflected into the WBC branch 8 while remaining RBCs flow to a bifurcation leading to the RBC branch 5, which strips off about 10% of the flow for fractional RBC counting with the remainder flowing directly to waste via the continuing channel 6. All branches release fluid to waste troughs 7 in the chip's support structure.

Figure 4:
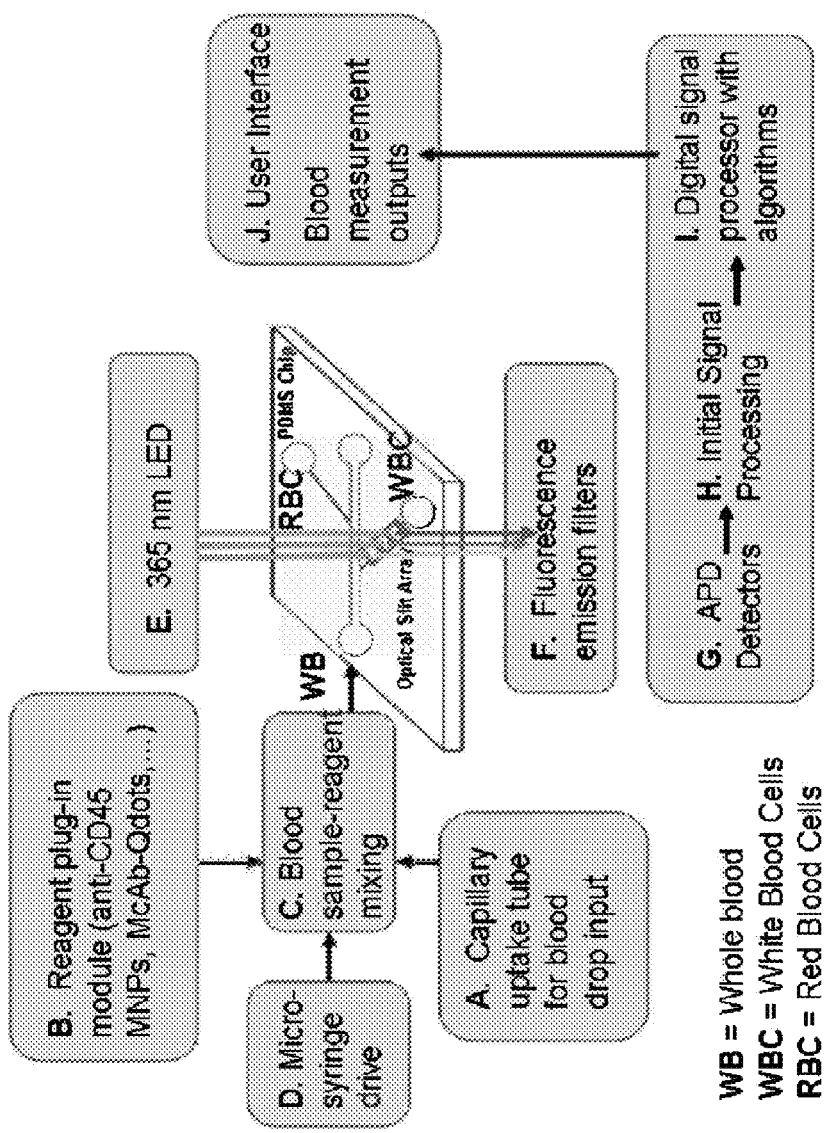
FIG. 4 is a schematic of an overall integrated design of the system showing subsystems with letter designations A-J, and a central PDMS microfluidics chip.

An overview of a miniature flow cytometer architecture is shown in FIG. 4 to help explain how the purposes just described are achieved on the basis of distinct Subsystems that surround the central microfluidics chip just described. The Subsystems are labeled "A" through "J" in FIG. 4. A description and purpose of each is given in the accompanying list.

A. Capillary tube for blood sampling is coated with heparin to prevent clotting of the drop of blood touched against the sampling port. The blood fills a capillary by capillary action and is measured (ca. 10 µL) in a metering valve, which resembles a stopcock.

B. The reagent cocktail (ca. 100 µL) is held in a small cylinder in the Single-Use Cartridge in a parallel track in the same metering valve as the sample.

C. Blood sample and reagent mixing occurs in a hybrid static mixer as both the blood and reagent emerge in parallel paths in the Single-Use Cartridge.

D. The pumps for sample and reagent are embodied in the Cartridge in the form of cylindrical reservoirs with pistons. The pistons are driven by the actuator within the Cytometer housing with the actuator having a single shaft for pushing the two pistons, one for driving buffer behind the sample and one for driving the reagent into the in-line mixer.

E. Four 365 nm LEDs are permanently installed in the optics stack within the Cytometer. Excitation light passes through a permanently installed IR filter and a system of lenses and is focused on the microchannels of the Cartridge. These LEDs are pulsed and synchronized with four phase-lock amplifiers that condition the fluorescence emission signals (see H, below). One diode laser illuminates the RBC channel to provide a light-scatter signal from all cells caused to flow down the narrow microfluidic channel.

F. Fluorescence emission filters for each emission wavelength are permanently installed in the optics paths. A simple lens system is also installed in the emission light path.

G. Four avalanche photodiodes (silicon photomultipliers) are mounted on the detector plane of the optics stack. These are positioned for optimum focus of the emitted fluorescence from the cells. A single PIN diode captures light scattered by cells in the RBC channel.

H. Four custom raw signal processing trans-impedance amplifiers are combined with phase-lock circuits for the four light paths to produce acceptable signals. The lock-in amplifiers are synchronized by the LED pulses.

I. Signal processing and electronics circuit boards receive, in parallel, output pulses from the four avalanche photodiodes and condition them for discrimination and counting by A/D conversion.

J. User interface and output display consist, respectively, of a starter microswitch operated by a thumb lever and an easy-to-read programmable digital display. Mechanical and electronic components are all independently programmable.

Example: Labeling Reagents for Cells to be Processed by the Embodiment

For the counting of the specified cell subtypes, T4, T8, and NK lymphocytes, the following Invitrogen reagents are specified:
Q10008 CD4, mouse anti-human, Qdot 605 conjugated
Q10152 CD8, mouse anti-human, Qdot 565 conjugated
Q10179 CD19, mouse anti-human, Qdot 655 conjugated
A less specific label for myeloid-derived cells can be selected, namely Qdot 655 for CD11b+ cells.

Optimization of Microfluidic Chip Subsystem Configuration and Fabrication Including Magnetic Deflection and Flow Balancing Example: Flow Channel Microfabrication Polydimethylsiloxane (PDMS) microchips were designed and manufactured using standard silicon photolithography to produce molds and soft lithography techniques to manufacture the PDMS chips in a cleanroom. Two-stage cytometer chips were designed using CAD-based program Autocad 2010 Student Version (Autodesk, Inc., San Raphael, Calif.). One example of the design consists of an incoming channel with, first, a branched channel into which the WBCs are magnetically deflected to an angle of 30° and a length of 35 mm to accommodate the optical analysis station dimensions. The RBC channel is just long enough (5 mm) to accommodate a single light-scatter sensing station. As a rule, the branched channels are one-third or less of the width of the main channel to ensure increased spacing between cells and appropriate passive RBC sorting. In an example of such a design all channels are designed to be 30 μm in height, although actual dimensions are slightly less due to photoresist processing. The magnet is 12.5 mm in length and occupies most of the incoming channel so that labeled WBCs begin to be deflected some distance upstream from the branch point at which they are collected.

Figure 5:
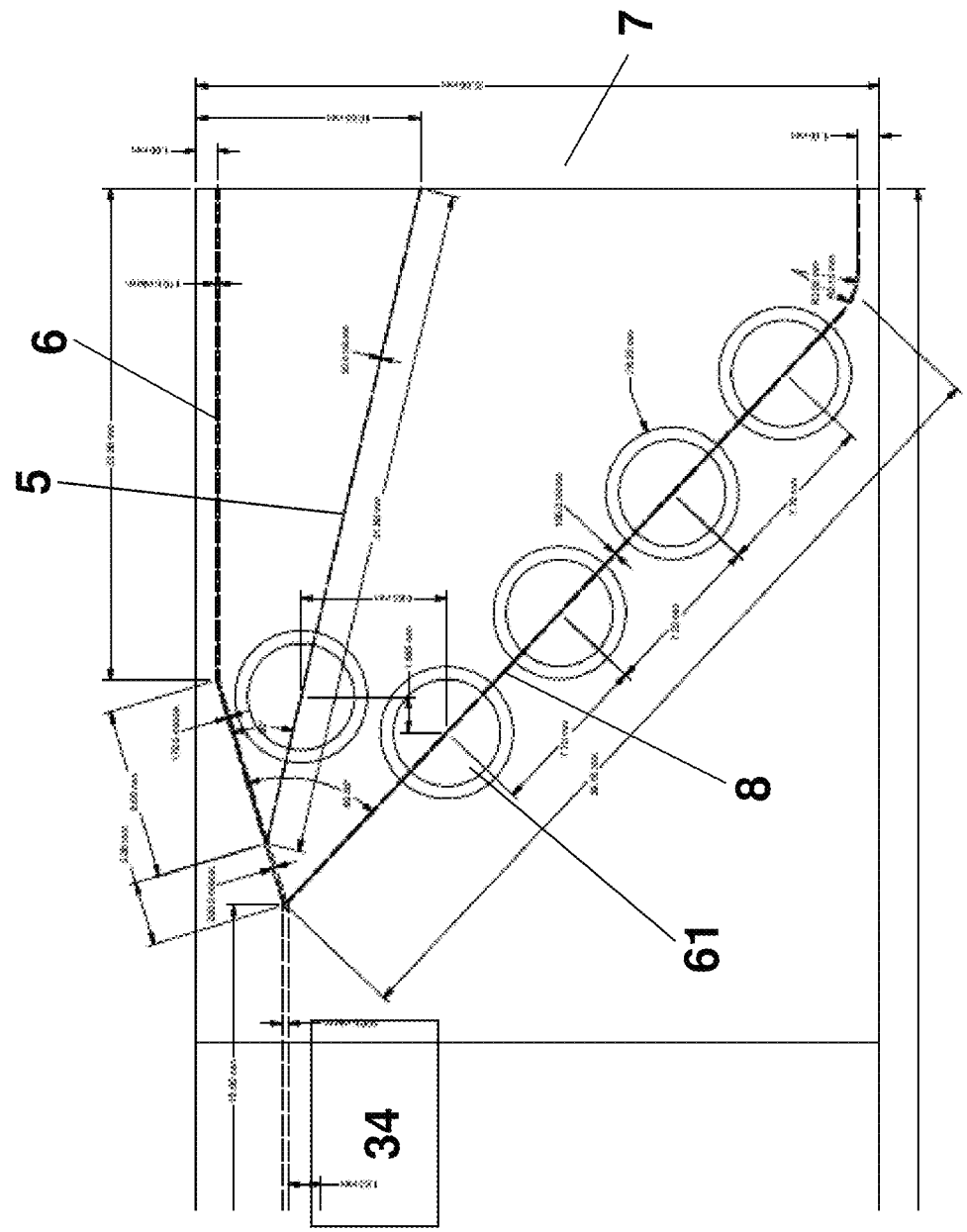
FIG. 5 is a dimensioned layout drawing of the microfluidics component of the integrated fluidics cartridge.

In a PDMS optical chip for blood analysis the initial channel 6 width at the top is 300 μm wide by 30 μm deep. The main channel branches to two channels, one that is 100 μm wide by 30 μm deep for the WBCs and another, 200 μm wide that branches in turn to the RBC counting channel 70 μm wide (similar to a standard flow cytometer nozzle) and maintains the 150 μm width for the final waste channel. Referring to FIG. 5, the larger circles are inlet and outlet ports, and these are sampled for verification of cell counts. The deflecting magnet (300 mT pole face field) is placed 7 mm upstream of the WBC channel. The 35 mm length of the WBC channel is designed to accommodate four fluorescence analysis stations as illustrated in FIG. 5.

The design of the microfluidics chip is shown superimposed on the flow cytometer reader's optical paths in FIG. 5. Its dimensions are selected to correspond to the optics layout plan and to the spatial constraints of the placement of the optical analysis components.

As illustrated in FIG. 5, circles 61 are not part of the cartridge design but are superimposed to show the positions of the five optical analysis stations. The channel branches are, from top to bottom in this particular embodiment, waste channel 6, RBC counting channel 5 and WBC counting channel 8. The WBC deflecting magnet will be positioned just below the incoming channel between the mixing reactor and the branch point 34.

Example: Performance Evaluation

Performance of the chip was evaluated by visual observation of fluorescent stained cells flowing through the device whilst situated upon an inverted fluorescent microscope stage. Pictures and videos were taken of the flowing particles using this method. The flow rate used was 10.0 μL/min, the design flow rate for a 12-minute blood analysis cycle; thus individual cells were not seen as spheres but as long trajectories through the entire single video frame. Images obtained under this condition provided excellent physics data for trajectory analysis. From the frames of the video it was seen that particles move through the channels along a constant streamline, according to the law of laminar flow. Groups of trajectories derived from single-frame video images showed that the spacing between two particles remains constant as they stay on their respective streamlines. This was predicted and forms part of the basis of designing a flow cytometer with no sheath flow—a departure from other microfluidic approaches. Drops observed at the outlets at the ends of the microchannels indicated that flow is proportional to channel cross section as designed and predicted. The WBC channel (100 μm), the waste channel (150 μm), and RBC channel (70 μm) produced drops in volumetric proportion to their respective flow rates.

Example: Test of Magnetic Deflection of Labeled Cells

WBCs were labeled with Bangs Labs BM588 BioMag anti-human CD45, 1.5 μm diameter magnetic spheres. The cells showed a magnetophoretic mobility of $1.19 \times 10^{-11}$ m$^3$/TAs while that of the free particles was $8.43 \times 10^{-12}$ m$^3$/TAs. From the ratio of these mobilities it is inferred that the average WBC was labeled with 11.5 magnetic particles. In an astonishingly simple relationship in which N is the number of particles per cell, and m is mobility and d is diameter, $$N = m_{cell} d_{cell} / m_{particle} d_{particle}$$

so that N=$(1.19 \times 10^{-11})(12\ \mu m)/(8.43 \times 10^{-12})(1.5\ \mu m)$=11.5 particles per cell.

Magnetic fields of the magnets were mapped along four axes: outward from the center of the small pole face, outward from the corner of the small pole face, outward at a 45° angle from the corner of the small pole face, outward at 90° angle from the corner of the small pole face. Plots of field strengths were derived from a map showing a field strength of 275 mT at the pole face corner (close to the calculated design value of 300 mT) and a 128 mT field 1 mm away at the far side of the microfluidic channel where the magnetic force acts on labeled cells. The ponderomotive force (magnetic energy gradient) experienced by a paramagnetic particle is estimated to be $B \cdot \nabla B = 17.4$ T$^2$/m. This exceeds the calculated requirement of $B \cdot \nabla B = 14$ T$^2$/m based on the measured magnetophoretic mobility of the magnetized WBCs just mentioned.

Magnet configurations were tested for the deflection of labeled WBCs into a lateral microfluidic channel using the custom NdBFe magnets. According to calculations a permanent 300 mT ceramic magnet positioned below the disposable PDMS chip can be expected to deflect a significant fraction of the white blood cells down the microfluidic channel where these WBCs will be counted on the basis of nuclear fluorescence and further examined for their Q-dot-antibody fluorescence. In practice it is only necessary to obtain a reproducible fraction of the total WBC and a statistically significant number of each cell subpopulation of interest to allow estimation of the WBC subsets with 95 percent confidence limits. Nevertheless, calculations indicated that, at reasonably expected microfluidic flow rates, all magnetically labeled cells should be captured from across the entire 300 μm flow channel width.

Particles were pumped through the channels using a syringe drive (Baby Bee Syringe Drive, BASi, West Lafayette, Ind.) at a rate of 10.0 μL/min with calculated speeds in the designed blood analysis chip of about 55 mm/sec in the wide main channel. According to the above calculations a permanent 300 mT ceramic magnet positioned below the disposable PDMS chip will divert a significant fraction of the white blood cells down the microfluidic channel where the WBCs are to be counted.

Fixed WBCs were labeled with Hoechst 33342 and 1.5 μm anti-human CD45 magnetic beads, and video clips were made. Two magnet positions were tested, and it became clear that placing the magnet at the same vertical level (i.e., in the same plane) as the channel during 10 μL/min flow rate deflected more WBCs than when positioned below the chip. A cluster of several trajectories was seen reflecting the classical expectation and represents the majority of observed trajectories in which the magnet pulls the cell across the channel into the streamline that is destined for the WBC branch. Roughly half of all fluorescent cells in the sample were captured magnetically in this test; the other cells were either too far from the magnet, too weakly labeled or not CD45 positive. Incidentally no RBC's were visible in the fluorescence images; therefore, RBC's will definitely not interfere with the WBC count.

Example: Construction of Sample and Reagent Applicator Components

The system design has the PDMS microfluidics chip just described and tested connecting to the blood and reagent reservoir and processing system, which locks into a pair of actuators that drive the flow of the 110 μL suspension out of the sample and reagent reservoirs in valve 15 and into a special static mixer and thence into the microfluidic channels. The described molded components, the pressure inlet hole, reagent metering valve, sample metering valve, static mixer/reactor compartments were integrated into the final design that was fabricated. Materials selections for fabrication of multiple copies are based on SLA materials that could meet strength and clarity requirements. The sample and reagent volumes are forced, side-by-side to flow into the 6-stage static mixer. The driving force is the two channels of buffer flow induced by the actuator drive, which pushes two pistons at the same velocity. The cross section of the sample channel is $\frac{1}{10}^{th}$ the cross section of the reagent channel so that, for example, 1 μL of sample is combined with every 10 μL of reagent as the fluids enter the mixer. Reagent and buffer are to be loaded by the manufacturer prior to sale. The user adds sample.

Figure 6:
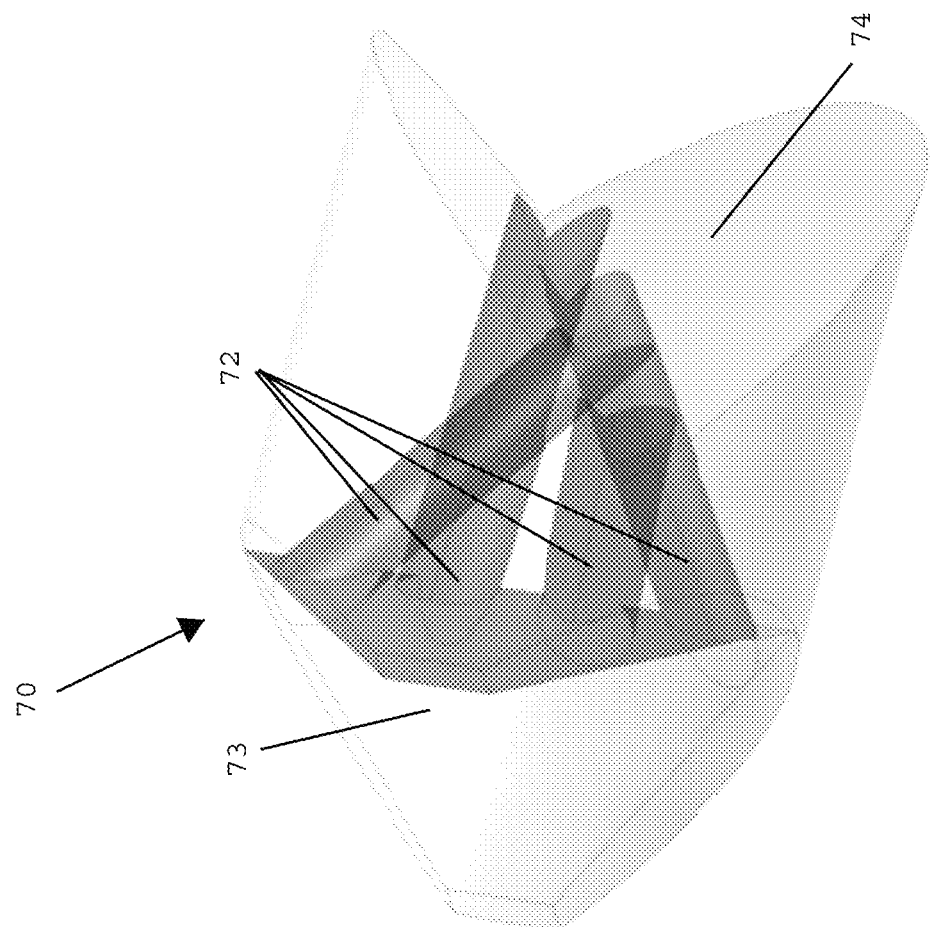
FIG. 6 is a single stage of the ISG static mixer.

The static mixer design finally selected is called an Interfacial Surface Generator (ISG). This design is available commercially from Ross Static Mixers, Hauppauge, N.Y.; however no commercial mixer is available in the 100 μL volume range. Each mixing element has four channels connecting tetrahedral chambers (FIG. 6). This brings the fluid from the four channels together in parallel "bands", so that the first mixing stage produces 8 bands of the 2 fluids, the next stage rotates the bands 90° and passes them to the next chamber in 32 bands etc. so there will be $2 \times 4^n$ bands in the nth stage. A 6-stage mixer results in 8,192 bands with a calculated maximum unmixed fluid width of $1000/8192 = 0.12$ μm, or less than $\frac{1}{10}^{th}$ the diffusion distance of a whole cell in 1 second (keeping in mind that a whole cell is generally considered "non-Brownian").

In the static mixer single stage 70 shown in FIG. 6, fluid enters four channels 72 aligned on a vertical edge of the left tetrahedral chamber 73. Fluid is deflected by the four channels so that it emerges from the four channels aligned on the horizontal edge of the right tetrahedral chamber 74. Stratum thicknesses are reduced by $2 \times 4^n$ rafter n stages.

All surfaces were routinely PEG coated making them extremely wettable. This is the final wetting method of choice. To make 100 mL of wetting reagent combine 0.123 g of boric acid ($H_3BO_3$, FW=61.8), 1 g PEG1000 in 100 mL PBS. This solution has a pH close to 7.0 and wets both the plastic and PDMS channels.

In visual testing of this static mixer yellow and blue dye solutions were pumped separately into the reagent and sample inlet channels, and the appearance of mixing resulting in green color was photographed. The sequence showed that after the $4^{th}$ mixing stage no yellow or blue was visible and the fluid in subsequent stages was green.

An actuator-operated piston pump that locks into the sample-reagent-buffer stream drives all fluids through the system. A test version of the cartridge was fabricated for the testing of this system with respect to bubble-free operation. The engagement and operation of the actuator motor and the fitting of the cartridge into the cytometer tray were followed by operation of the actuator motor to drive pistons 13 shown in FIG. 1.

Figure 2:
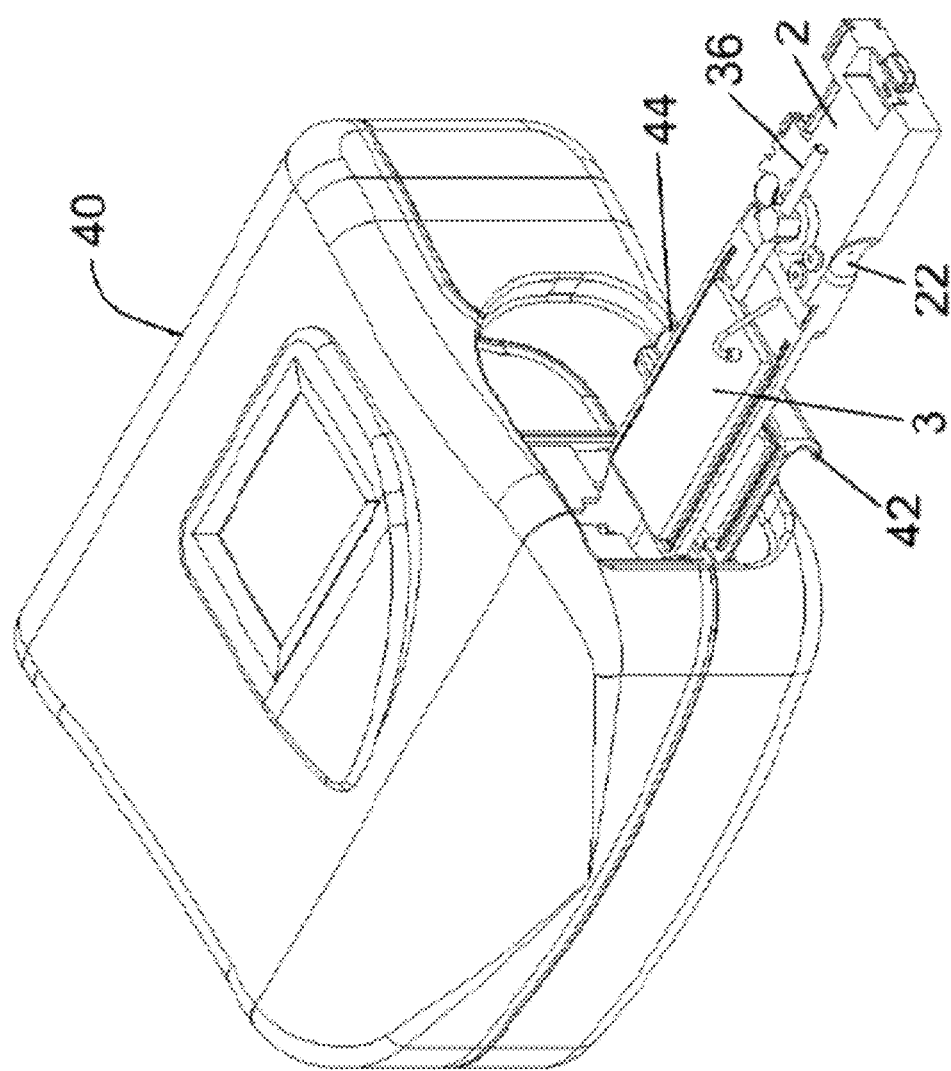
FIG. 2 is the cell processing cartridge of FIG. 1 being inserted into a miniature cytometer reader system.

The ergonomics of cartridge insertion were carefully worked out. The user opens the cartridge tray door. FIG. 2 shows the cartridge with the metering valve in the operating position. The cartridge will not pass through the tray entrance in the storage condition. The user then places a drop of blood (or other sample) at the capillary opening and the blood is drawn into the metering valve, which is then rotated 90 degrees in the only direction allowed due to a mechanical detent. This 90-degree rotation now allows the handle of the metering valve to pass through the slot in the tray entrance (FIG. 2). The entrance has beveled sides to guide the cartridge precisely onto the rails of the tray. When the cartridge is inserted all the way in, the door cannot be closed until the thumb tab 24 is removed. The purpose of the thumb tab is to prevent accidental actuation of the plungers in the buffer cylinders 10 and 12. The actuator shaft can only operate the pistons 13 when the thumb tab has been removed, and the door 42 of the cytometer can only be closed when the thumb tab has been removed. After the thumb tab has been removed the operator closes the door and rotates a thumb lock 44 which assures the door is closed light-tight due to a wedge on the face of the cytometer door. Rotating the thumb lock prevents the door from being re-opened but, more importantly, rotates the deflecting magnet into its detent in the underside of the cartridge at position 34. This movement of the magnet closer to the cartridge assures adequate proximity (owing to the short range of the magnetic ponderomotive force) for the deflection of the magnetically labeled WBCs as described above in detail. A single power button then initiates the software controlled cycle of the processing and analysis of the sample. All of these maneuvers are considered to be gravity independent and safe and without pinch hazard.

Example: Loading of Reagent and Sample into the Metering Valve

The loading of fluid by the vendor will follow the following procedure: Rotate the metering valve 15 to the OPERATE position and remove the removable piston protector (aka thumb tab 24). Remove the buffer pistons 13 from the cylinders 10 and 12, and place the cartridge on edge with the buffer cylinder openings facing upward. With a syringe, squirt 500 µL of wetting solution (PEG1000 plus borate in PBS) into the reagent septum 20 until this solution fills the buffer pistons. Tap gently to remove visible bubbles. Allow this solution to stand overnight at 37° C. in a controlled incubator. Remove this solution by placing a needle in the reagent septum and holding the cartridge vertical to allow the solution to drain. Blot excess fluid with a Kimwipe. Blow a stream of clean, dry air through the same needle using a "canned air" cleaner and observe the loss of moisture from the fluid path. Allow this fluid path to dry for 3 hours. Rotate the valve handle 36 to the STORAGE AND SAMPLE LOAD position before installing sample vent 23. Using a syringe and needle or fine-tipped micropipette, force about 40 µL of CTAB solution into the sample capillary with the sample vent removed. Avoid forming bubbles. Allow to stand at room temperature for 3 hours. Flush the pathway with 100 µL of distilled water. Fill the pathway using about 100 µL of heparin solution (20 USP Units/mL in PBS). Allow to stand 3 hours. Flush the heparin solution out of the pathway with a stream of canned air. Allow to dry for 1 hour. Install the sample vent filter 23. Rotate the metering valve to the OPERATE position and again set the unit on edge with the open cylinders facing upward. Flood the fluid paths with PBS and install the buffer pistons without forming bubbles. Slide the removable piston protector (aka thumb tab) into position as far as it will go while maintaining the pistons as close to the tab as possible. Rotate the valve handle to the REAGENT LOAD position. Force existing buffer out of the reagent pathway and follow with a stream of dry canned air through a syringe needle. Install the reagent vent filter 21. With a syringe and needle fill the reagent pathway with reagent solution until the liquid just reaches the reagent vent. Rotate the valve handle to the STORAGE AND SAMPLE LOAD position. Seal in a vapor-proof bag and store at 4-8° C. At present the reagent cannot be guaranteed beyond 2 weeks of storage at this temperature. Do not freeze.

The loading of sample by the user will proceed as follows. Place a drop of very fresh (within one minute) blood, approximately 40 µL, on the surface of the cartridge at the capillary opening. Notice that the blood is drawn all the way into the capillary and does not flow out either end of the capillary. Rotate the valve handle 90 degrees to the OPERATE position. Open the cartridge tray door 42 and slide the cartridge 1 in as far as it will go. Remove the thumb tab 24 from the cartridge so the door can be closed. Close the door and rotate the thumb lock 44 to its full upright position against the door making sure the door is tightly closed (it should be light-tight). Allow the automated cytometer to do its job without being moved for about 1 hour. Watch for the appearance of counts on the display after 20 minutes. When counting ceases and there are no further increases in any of the cell counts open the door and carefully remove the cartridge (there will be fluid in the waste gutters) and seal the cartridge in a biohazard bag for disposal.

Example: Test of Blood Cell Labeling

Whole blood and reagents were successfully mixed using the hybrid static in-line mixer. The cartridge was activated by the actuator pump without installing into the housing. The reagent mixture was exactly as given above, and blood was freshly drawn under IRB-approved protocol, anticoagulated and entered into the sample stream by capillary action as specified in the previous application section.

Reagent was added through the reagent channel 19, blood entered the blood capillary 22, the metering valve was rotated 90 degrees, the actuator motor was started, the buffer pistons advanced forcing blood and reagent to meet at the combining channel 29 and advance to the static mixer 28 and flow toward the microfluidic PDMS downstream chip 3. The cartridge was 3.8 cm (1.5") wide.

The efficacy of the mixer was tested by head-to-head comparison with the standard laboratory procedure. A 10:1 reagent:sample volume ratio with all reagents present at their specified concentrations was used. Reagents and sample were combined in a 1.5 mL Eppendorf tube and designated "Test Tube". Pumps operated at a combined flow rate of 10 µL/min for 45 minutes, including time to clear the volume of wetting solution from the mixer. The effluents from the mixer were collected at the mixer outlet. The results were compared using an iCyte® flow cytometer with excitation at 405 nm and filters set for the emissions of Hoechst 33342 and the Qdots. The raw data from the iCyte flow cytometer were analyzed in software by first setting two criteria for identifying WBCs: they should be stained with Hoechst 33342, and they should have the combined forward and side light scatter of WBCs. Using these two gates and subtracting "spillover" counts due to Hoechst dye at the Qdot counting wavelengths (typically 13-30% of the total fluorescence at each wavelength) the total number of counts of CD11b, CD4, and CD8 cells were calculated and normalized to the percent of total counting events in each case. The resulting calculations from the raw data are displayed in Table 1, in which it is seen that the normalized counts are consistent between the two methods, within experimental error and that the counts are within expected values. This result is considered to indicate the mixer design and its implementation are acceptable. In the Test Tube experiment the numbers are percent of each cell type in a total of 1,000,000 events; in the case of the Static Mixer the total number of events was 41,553. The labeling results by the two methods are in substantial agreement. It includes the formulation of reagent mixtures, the loading of reagent, and the loading of sample.

TABLE 1

Comparison of Test Tube and Static Mixer labeling results.

| Experiment ratio | CD11b | CD4 | CD8 | CD11b + CD4 + CD8 | CD11b/CD8 |
|---|---|---|---|---|---|
| Test tube | 0.057 | 0.029 | 0.054 | 0.140 | 1.2/1.0 |
| Static mixer | 0.046 | 0.013 | 0.051 | 0.106 | 0.92/1.0 |

Example: Microfluidic Multichannel Flow Cytometer Integration for Use

The Microfluidic Multichannel Flow Cytometer is an integrated system that not only performs the functions of a flow cytometer but also the other functions of a cytometry laboratory, namely sample preparation. This version is designed to perform RBC and WBC counts on a drop of blood and to quantify three WBC subsets. There are two components, a Single-Use Cartridge and a Cytometer Reader. The Single-Use Cartridge contains all of the fluidics and accepts a drop of blood, dilutes it 10-fold into a pre-loaded reagent cocktail, labels the cells in a static mixer, pumps the cells through microfluidic channels for counting and collects the effluent waste liquid. The Cytometer Reader contains all of the electronics and mechanics of the cytometer and no fluidics. The Cartridge is inserted by the user into the Cytometer Reader, which includes an actuator that operates the pistons in the Cartridge to pump the fluids, controlling electronics for switching functions on and off, five optical analysis stations for counting the five cell types, electronic pulse processing for the optical signals, and a five-channel pulse counter and display of counts of the five cell types. With the appropriate reagent cocktail the current version will display counts of RBCs, WBCs (based on nuclear staining), T4 and T8 lymphocytes, and granulocytes.

The microfluidics chip itself consists of an inlet channel for the blood-reagent mixture, a magnetic deflector that drives magnetically labeled WBCs down the WBC channel, and a continuation of the inlet channel that is bifurcated approximately 5:1 to sample the total cell count (essentially the RBC count).

Single-Use Cartridge

The microfluidic channels (shown in FIG. 1) are connected via transport tube 27 to the blood and reagent reservoir system, which locks into an actuator that drives the flow of the 10 and 100 µL suspensions out of the sample and reagent reservoirs, respectively (within the rotating valve 15) and into the special 6-stage static mixer 28 and thence into the microfluidic channels. The rotating stopcock is set to the "operate" position so that the sample and reagent are forced, side-by-side to flow into the static mixer. The driving force is the two channels of buffer flow from the pistons induced by the actuator drive, which pushes two pistons at the same velocity. The cross section of the sample channel is $1/10^{th}$ the cross section of the reagent channel so that, for example, 1 µL of sample is combined with every 10 µL of reagent as the fluids enter the mixer. Reagent and buffer are to be loaded by the manufacturer via the reagent septum prior to sale. The user adds the sample, which consists of at least 20-30 µL of blood, typically from a finger stick.

Blood Cell Labeling with Magnetic and Quantum-Dot Reagents

The following protocol is used for formulating specific labeling reagents for WBCs, T4 lymphocytes, T8 lymphocytes and granulocytes.

Stock solution 1. Heparin, 20 USP Units/mL:
 Weigh 5 mg heparin (212 USP Units/mg, Sigma H3393-100KU 119K1581)
 Dissolve in 5.0 mL PBS
 Store Refrigerated
Stock solution 2. Hoechst 33342, 1 µg/mL
 Dilute 20 µL Hoechst 33342 (InVitrogenFluopure, 10 mg/mL solution, H3570)
 Into 10.0 mL PBS
 Store Refrigerated
To make 5.15 mL of labeling cocktail
 4.5 mL Heparin stock solution
 0.5 mL Polysciences anti-human CD45 biomag beads 85045-5
 50 µL InVitrogen anti-human CD4 Qdot 655 Q10007
 50 µL InVitrogen anti-human CD8 Qdot 705 Q10059
 50 µL eBioscienceeFluor anti-human CD11b 605NC 50 µL Hoechst stock solution
This solution is isotonic and anticoagulative. It can be noted that the volume is enough for about 20 tests.

Succinct Description of Operations

The engagement and operation of the actuator motor and the fitting of the cartridge into the cartridge tray are initiated by insertion of the cartridge as illustrated in the rendering shown in FIG. 2.

Basic operating components of the cartridge are:
Metering valve for loading reagent solution by supplier: 100 µL
Metering valve for loading sample by user: 10 µl
Feeds and exits for both metering valves
Pressure inlet for pumping
Connection to microfluidics chip
Microfluidics chip with
 Single channel to receive sample
 33% bifurcation to receive magnetically deflected WBCs
 10% bifurcation to sample RBC count
 Termination in an absorbent strip to accommodate >200 µL waste solution Basic components of the miniature cytometer reader in which the contents of the cartridge are analyzed are:
Slot to accommodate cartridge mating to
 Four optical analysis stations for Hoechst 33342 and 3 quantum dots
 One optical analysis station for RBCs using light absorbance/scatter
 Pressure outlet (air or liquid) for pumping fluid through channels
Optical fluorescence analysis stations comprising of
 Superluminescent LED at 365 nm focused on microchannel with lens system
 Avalanche photodiode collecting fluorescence via slit, band-pass filter, lenses
 Synchronization for phase-lock amplification of APD output signal
 Gap between these for microfluidic chip
Optical RBC analysis comprising of
 Bright LED at 560 nm focused on microchannel with lens system
 PIN photodiode collecting 560 nm light through slit and lens system
Electronics comprising of
 Power supplies for LEDs, APDs, amplifiers, ADCs, CPU
 Pulse input to LEDs and phase-lock amplifiers for APDs
 Output pulse processing circuits, ADC channels CPU for accumulating pulse counts, controlling operation and displaying data
Display monitor for reporting RBC, WBC and WBC subset pulse counts
Rechargeable battery and charger
Means for cooling
Fluidics comprising of
Micropump capable of developing pressure for feed through cartridge
Means of initiating and terminating pumping (user switch)
Pathway and seal to articulate with cartridge
Housing comprising of
Space for electronics, surface display
Light-tight slot for receiving cartridge
Composition for EMI shielding
Ventilation for heat-sink and/or cooling fan
Preparation of Cartridge:
Heparinize blood metering valve with syringe or micropipet
Preload entire cartridge with borate buffer containing heparin
Flush sample metering valve with air, affix exit filter
Flush reagent metering valve with air, affix exit filter
Add reagent, rotate valve 45°
Blot excess reagent at air-pressure entrance
Store at 4-10 C
Reagent formulation:
Bangs anti-CD45 1.5 µm magnetic microspheres, $5 \times 10^6$ total particles
Anti-CD11b quantum dots, $10^7$-$10^8$ total particles
Anti CD4 quantum dots, $10^7$ total particles
Anti CD8 quantum dots, $10^7$ total particles
Hoechst 33342
Heparin
All qs to 100 µL in PBS
Cells to be stained:
Hoechst 33342: All WBCs, $10^5$ total max
Anti-CD45 magspheres: All WBCs, $10^5$ total max
AntiCD11b Qdots: All granulocytes, $0.5 \times 10^5$ total max
AntiCD4 Qdots: All T4 lymphocytes, $10^4$ total max
AntiCD8 Qdots: All T8 lymphocytes, $10^4$ total max While there has been described and illustrated particular embodiments of a novel apparatus and method, and in particular, a cell processing and flow cartridge that can be used in a miniature flow cytometer, it will be apparent to those skilled in the art that variations and modifications may be possible without deviating from the broad spirit and principle of the present embodiment, which shall be limited solely by the scope of the claims appended hereto.

The invention claimed is:

1. A cartridge comprising:
a microfluidic chip including:
a main channel,
a first channel branching directly off said main channel and a second channel branching directly off said main channel, wherein each one of said first channel and said second channel is downstream of and in fluid communication with said main channel; and
a fluid processing unit including:
an elastomer septum for adding volumes of reagents into said fluid processing unit of said cartridge,
a sample inlet for adding volumes of the suspension of cells into said fluid processing unit of said cartridge,
a static mixer for mixing the reagents with the suspension of cells, wherein said static mixer has multiple stages of interfacial surface generation, wherein each stage includes a first chamber, a second chamber, and at least two channels connecting said first chamber to said second chamber, wherein said first chamber is upstream relative to said second chamber,
a first buffer cylinder including a first piston positioned within, and
a second buffer cylinder including a second piston positioned within; and
wherein said first piston and said first buffer cylinder and said second piston and said second buffer cylinder are in fluid communication with said static mixer, said main channel, said first channel, and said second channel.

2. The cartridge of claim 1 in combination with a device having at least one light source and at least one light detector for counting cells, wherein when said cartridge is inserted into said device at least one of said at least two channels are positioned between said at least one light source and said at least one light detector.

3. The cartridge of claim 1 in which said fluid processing unit includes at least one rotating valve, said at least one rotating valve having at least one first channel for the reagents and at least one second channel for the suspension of cells, wherein said at least one first channel of at least one rotating valve is downstream of said second piston positioned within said second buffer cylinder and said at least one second channel of at least one rotating valve is downstream of said first piston positioned within said first buffer cylinder.

4. The cartridge of claim 3 wherein said at least one first channel of said at least one rotating valve includes a first volume of the reagents and said at least one second channel of said at least one rotating valve includes a second volume of the cell suspension.

5. The cartridge of claim 4 wherein said at least one first channel and said at least one second channel of said at least one rotating valve are rotated in common between at least a loading position and an operating position;
when said at least one rotating valve is in said loading position said at least one first channel of said at least one rotating valve is in fluid communication with said elastomer septum and said at least one second channel of said at least one rotating valve is in fluid communication with said sample inlet; and
when said at least one rotating valve is in said operating position said at least one first channel of said at least one rotating valve is in fluid communication with said second piston positioned within said second buffer cylinder and said static mixer and said at least one second channel of said at least one rotating valve is in fluid communication with said first piston positioned within said first buffer cylinder and said static mixer.

6. The cartridge of claim 1 wherein said static mixer has a volume between 0.1 and 0.4 milliliters.

7. The cartridge of claim 3 wherein said at least one first channel of said at least one rotating valve includes a certain volume of the reagents to be delivered towards said static mixer when said at least one rotating valve is in said operating position.

8. The cartridge of claim 2 wherein said device further comprises at least one magnet, wherein when said cartridge is inserted into said device said at least one magnet of said device is positioned adjacent said at least one main channel of said microfluidic chip to deflect magnetically labeled cells into at least one of said first channel and said second channel of said microfluidic chip.

9. The cartridge of claim 3 wherein said second buffer cylinder includes a first volume in fluid communication with said at least one first channel of said at least one rotating valve and said first buffer cylinder includes a second volume in fluid communication with said at least one second channel of said at least one rotating valve.

10. The cartridge of claim 5 wherein when said at least one rotating valve is in said operating position said elastomer septum is not in fluid communication with said at least one first channel of said at least one rotating valve and said sample inlet is not in fluid communication with said at least one second channel of said at least one rotating valve.

11. The cartridge of claim 3 wherein said at least one second channel of said at least one rotating valve includes a certain volume of the suspension of cells to be delivered towards said static mixer when said at least one rotating valve is in said operating position.

12. The cartridge of claim 1 further comprising a push-bar, wherein said push-bar couples to both said first piston and said second piston, wherein said first piston, said second piston, and said push-bar travel together relative to said first buffer cylinder and said second buffer cylinder at substantially the same velocity.

\* \* \* \* \*